United States Patent
Kostrzewski

(10) Patent No.: US 10,251,645 B2
(45) Date of Patent: Apr. 9, 2019

(54) SURGICAL FASTENING WITH W-SHAPED SURGICAL FASTENERS

(71) Applicant: Covidien LP, Mansfield, MA (US)

(72) Inventor: Stanislaw Kostrzewski, Newtown, CT (US)

(73) Assignee: Covidien LP, Mansfield, MA (US)

( * ) Notice: Subject to any disclaimer, the term of this patent is extended or adjusted under 35 U.S.C. 154(b) by 367 days.

(21) Appl. No.: 15/181,767

(22) Filed: Jun. 14, 2016

(65) Prior Publication Data

US 2017/0354408 A1    Dec. 14, 2017

(51) Int. Cl.

| A61B 17/04 | (2006.01) |
|---|---|
| A61B 17/10 | (2006.01) |
| A61B 17/068 | (2006.01) |
| A61N 5/10 | (2006.01) |
| A61B 17/064 | (2006.01) |
| A61B 34/30 | (2016.01) |
| A61B 34/37 | (2016.01) |
| A61B 90/00 | (2016.01) |
| A61B 34/00 | (2016.01) |

(52) U.S. Cl.
CPC ........ *A61B 17/068* (2013.01); *A61B 17/0644* (2013.01); *A61B 17/0684* (2013.01); *A61B 17/105* (2013.01); *A61B 34/30* (2016.02); *A61B 34/37* (2016.02); *A61N 5/1001* (2013.01); *A61N 5/1007* (2013.01); *A61N 5/1027* (2013.01); *A61B 2034/302* (2016.02); *A61B 2034/742* (2016.02); *A61B 2090/392* (2016.02); *A61N 2005/1011* (2013.01); *A61N 2005/1019* (2013.01)

(58) Field of Classification Search
CPC .... A61B 17/07207; A61B 2017/07271; A61B 2017/07278; A61B 17/072; A61B 17/068; A61B 17/1155; A61B 17/105
USPC ........................ 227/175.1–182.1; 606/19–221
See application file for complete search history.

(56) References Cited

U.S. PATENT DOCUMENTS

| 4,526,174 A | * | 7/1985 | Froehlich ........... A61B 17/0684 206/438 |
|---|---|---|---|
| 4,655,222 A | * | 4/1987 | Florez .................... A61L 31/10 411/920 |
| 4,669,647 A | | 6/1987 | Storace |

(Continued)

FOREIGN PATENT DOCUMENTS

WO    02/19920 A1    3/2002

OTHER PUBLICATIONS

Extended European Search Report issued in corresponding European Application No. 17175562.2 dated Feb. 14, 2018.

*Primary Examiner* — Robert Long

(57) ABSTRACT

An end effector for a surgical fastening device is provided. The end effector includes a body defining a longitudinal axis, one or more fasteners, an anvil, and a pusher. Each fastener has an unformed configuration and a formed configuration. Each fastener includes first and second arms that extend in opposite directions. The first arm has first and second elbow segments. The first elbow segment is configured to bend as the fastener is formed. The second elbow segment is configured to remain unbent as the fastener is formed. The pusher is configured to advance the fastener distally through the body and into engagement with the anvil to form the fastener against the anvil.

20 Claims, 10 Drawing Sheets

(56) References Cited

U.S. PATENT DOCUMENTS

| | | | | |
|---|---|---|---|---|
| 4,706,864 A * | 11/1987 | Jacobsen | B25C 1/001 | 227/109 |
| 4,787,387 A * | 11/1988 | Burbank, III | A61B 17/0644 | 227/176.1 |
| 4,887,601 A * | 12/1989 | Richards | A61B 17/0644 | 606/219 |
| 4,930,674 A * | 6/1990 | Barak | A61B 17/072 | 227/179.1 |
| 5,282,829 A * | 2/1994 | Hermes | A61B 17/064 | 411/479 |
| 5,389,098 A * | 2/1995 | Tsuruta | A61B 17/00234 | 606/142 |
| 5,413,584 A | 5/1995 | Schulze | | |
| 5,573,543 A * | 11/1996 | Akopov | A61B 17/04 | 227/175.1 |
| 5,582,616 A * | 12/1996 | Bolduc | A61B 17/064 | 606/139 |
| 5,586,711 A * | 12/1996 | Plyley | A61B 17/064 | 227/176.1 |
| 6,059,787 A * | 5/2000 | Allen | A61B 17/0642 | 606/75 |
| 6,981,983 B1 * | 1/2006 | Rosenblatt | A61B 17/0401 | 128/898 |
| 7,918,873 B2 * | 4/2011 | Cummins | A61B 17/0644 | 606/219 |
| 8,240,538 B1 * | 8/2012 | Manoux | A61B 17/07207 | 227/178.1 |
| 9,289,207 B2 * | 3/2016 | Shelton, IV | A61B 17/1114 | |
| 9,750,502 B2 * | 9/2017 | Scirica | A61B 17/0644 | |
| 9,775,623 B2 * | 10/2017 | Zammataro | A61B 17/1285 | |
| 9,833,241 B2 * | 12/2017 | Huitema | G06F 11/1425 | |
| 9,848,874 B2 * | 12/2017 | Kostrzewski | A61B 17/0644 | |
| 9,872,683 B2 * | 1/2018 | Hopkins | A61B 17/07207 | |
| 2002/0049472 A1 * | 4/2002 | Coleman | A61B 17/0057 | 606/219 |
| 2004/0006372 A1 * | 1/2004 | Racenet | A61B 17/0644 | 606/219 |
| 2006/0235469 A1 * | 10/2006 | Viola | A61B 17/064 | 606/219 |
| 2007/0244351 A1 * | 10/2007 | Wazer | A61B 17/0644 | 600/3 |
| 2008/0082124 A1 * | 4/2008 | Hess | A61B 17/064 | 606/219 |
| 2009/0001121 A1 * | 1/2009 | Hess | A61B 17/064 | 227/175.1 |
| 2009/0062799 A1 * | 3/2009 | Holsten | A61B 17/0644 | 606/75 |
| 2009/0255976 A1 * | 10/2009 | Marczyk | A61B 17/072 | 227/178.1 |
| 2009/0255978 A1 * | 10/2009 | Viola | A61B 17/0644 | 227/180.1 |
| 2009/0272783 A1 * | 11/2009 | Crainich | A61B 17/0644 | 227/176.1 |
| 2009/0277946 A1 * | 11/2009 | Marczyk | A61B 17/0644 | 227/176.1 |
| 2009/0277948 A1 * | 11/2009 | Beardsley | A61B 17/0644 | 227/178.1 |
| 2009/0281554 A1 * | 11/2009 | Viola | A61B 17/0644 | 606/142 |
| 2010/0191258 A1 | 7/2010 | Harris et al. | | |
| 2010/0237128 A1 * | 9/2010 | Miller | A61B 17/0642 | 227/175.1 |
| 2011/0245578 A1 * | 10/2011 | Wazer | A61B 17/0644 | 600/3 |
| 2012/0193398 A1 * | 8/2012 | Williams | A61B 17/0644 | 227/179.1 |
| 2012/0289762 A1 * | 11/2012 | Shariati | A61B 17/064 | 600/7 |
| 2013/0214025 A1 | 8/2013 | Zemlok et al. | | |
| 2014/0131418 A1 | 5/2014 | Kostrzewski | | |
| 2014/0144968 A1 * | 5/2014 | Shelton, IV | A61B 17/1114 | 227/175.1 |
| 2015/0005789 A1 | 1/2015 | Sniffin et al. | | |
| 2015/0297199 A1 | 10/2015 | Nicholas et al. | | |
| 2016/0345973 A1 * | 12/2016 | Marczyk | A61B 17/07207 | |

\* cited by examiner

SURGICAL FASTENING WITH W-SHAPED SURGICAL FASTENERS

TECHNICAL FIELD

The present disclosure relates to surgical devices, systems, and/or methods for performing surgical procedures. More specifically, the present disclosure relates to surgical fastener applying devices and/or systems that are loadable with end effectors containing absorbable or permanent surgical fasteners for performing brachytherapy, and methods of use thereof.

BACKGROUND

Brachytherapy is a general term for medical treatment that involves temporary or permanent placement of radioactive sources near targeted locations of diseased tissue in the body of a patient. This targeted delivery of radioactive sources helps eliminate the diseased tissue while minimizing radiation exposure to healthy tissue. Exemplary radioactive sources include radioactive seeds, radioactive rods and radioactive coils.

The implantation of radioactive sources for brachytherapy may be carried out using minimally invasive techniques such endoscopy or laparoscopy. Laparoscopic and endoscopic procedures generally utilize long and narrow devices capable of reaching remote regions within the body accessed through surgical portal apparatus disposed in incised tissue. These devices may also be advanced through natural body openings.

Accordingly, there is a need to develop improved systems, devices, and methods for targeted delivery of brachytherapy.

SUMMARY

According to one aspect of the present disclosure, a surgical device is provided. The surgical device includes an end effector for a surgical fastening device. The end effector comprises a body defining a longitudinal axis, one or more fasteners, an anvil, and a pusher. The pusher is configured to advance the one or more fasteners distally through the body and into engagement with the anvil to form the one or more fasteners against the anvil.

The anvil may be pivotally coupled to the body and movable between a first position and a second position. The anvil may be configured to engage the one or more fasteners while in the first position and to disengage from the one or more fasteners while in the second position.

The one or more fasteners have an unformed configuration and a formed configuration. Each fastener may include first and second arms. The first and second arms may extend in opposite directions. The first arm may include first and second elbow segments. The first elbow segment may be configured to bend as the fastener is formed. The second elbow segment may be configured to remain unbent as the fastener is formed.

The one or more fasteners may include a backspan that extends between the first and second arms. The anvil may be engagable with the backspan to form the first and second arms about the backspan. The anvil may include a lip. The lip may define a fastener forming surface configured to contact the backspan so that the first and second arms can pivot about the anvil to form the one or more fasteners. In some embodiments, the backspan may support a radioactive source.

In certain embodiments, the end effector may further include an anvil release cam that is selectively engagable with the anvil to separate the anvil from engagement with the one or more fasteners after the one or more fasteners are formed.

In some embodiment, the pusher may include a notch formed in a distal end thereof. The notch may be configured to receive the one or more fasteners therein.

The end effector may further comprise a firing bar that is axially translatable to axially translate the pusher. The firing bar and the pusher may be spring biased by one or more springs. The one or more springs may include a first spring and a second spring. The first spring may have a different spring rate than the second spring.

According to another aspect of the present disclosure, a fastener for a surgical fastening device is provided. The fastener comprises a backspan having a first end and a second end opposite to the first end, a first arm extending from the first end of the backspan, and a second arm extending from the second end of the backspan. The backspan may support a radioactive source. The first and second arms may be movable relative to the backspan from an unformed configuration to a formed configuration. The fastener may have more than three sides while the first and second arms are in the unformed configuration and three sides while the first and second arms are in the formed configuration.

In some embodiments, each of the first and second arms may include a crossing segment and a tissue engaging segment. As the first and second arms are moved from the unformed configuration to the formed configuration, the crossing segments of the first and second arms may converge toward the backspan and the tissue engaging segments of the first and second arms may converge toward one another.

In certain embodiments, the crossing segments are connected to the tissue engaging segments of the respective first and second arms by elbow segments.

In some embodiments, the radioactive source may be supported between the three sides of the fastener when the first and second arms are in the formed state. In certain embodiments, the radioactive source may be in the form of an isotope capsule surrounding the backspan.

In certain embodiments, the backspan, the first arm, the second arm, or combinations thereof, may include titanium wire.

According to yet another aspect of the present disclosure, a surgical fastening device is provided. The surgical fastening device comprises a handle assembly, an elongated body portion that extends distally from the handle assembly and defines a longitudinal axis, and an end effector supported on a distal end of the elongated body portion. The end effector may include a body, one or more fasteners having a backspan and a pair of legs extending from the backspan, and an anvil that is pivotable between a first position and a second position. The anvil may be configured to selectively engage the backspan of the one or more fasteners to form the one or more fasteners while in the first position. The anvil may be pivotable to the second position to enable the one or more fasteners to dispense from the body after being formed.

In certain embodiments, the one or more fasteners may include stacked fasteners that are positioned for sequential firing.

The surgical fastening device may further include a pusher defining a notch that is selectively engagable with a pair of elbow segments of each fastener of the stacked fasteners.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description given below, serve to explain the principles of the disclosure, wherein:

FIG. 11 illustrates the fastener of FIG. 7 being fired into tissue by the end effector of FIG. 2;

DETAILED DESCRIPTION

Figure 1:
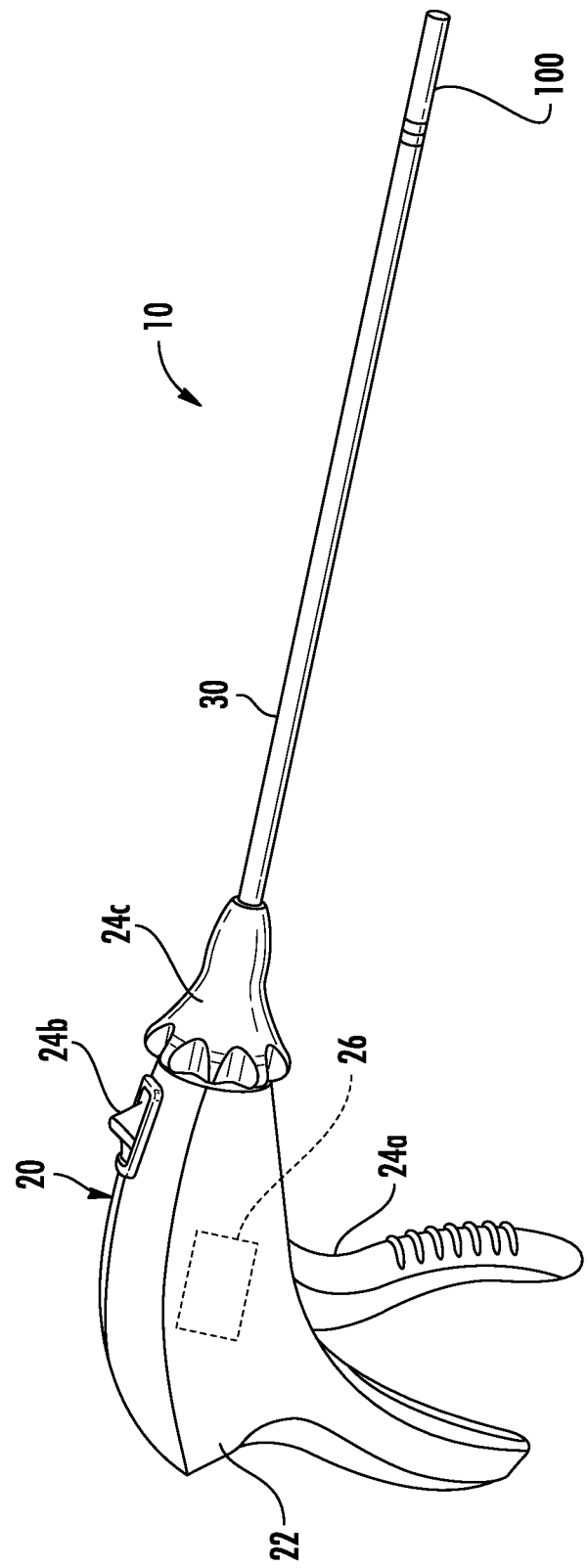
FIG. 1 is a perspective view of an endoscopic surgical system in accordance with the present disclosure.

Embodiments of the presently disclosed devices are described in detail with reference to the drawings, in which like reference numerals designate identical or corresponding elements in each of the several views. As used herein, the term "distal" refers to that portion of the device that is farther from the user, while the term "proximal" refers to that portion of the device that is closer to the user. As used herein, the term "clinician" refers to a doctor, nurse, or other care provider and may include support personnel. In the following description, well-known functions or constructions are not described in detail to avoid obscuring the present disclosure in unnecessary detail.

Non-limiting examples of endoscopic surgical devices according to the present disclosure include mechanical and/or electromechanical devices such as surgical staplers, surgical tack appliers (i.e., tackers), and the like. One particular example includes Medtronic's Endo GIA™ Stapler. For a more detailed description of similar endoscopic surgical devices and components thereof that can be used with, or adapted for use with, the presently described endoscopic surgical devices, reference can be made to U.S. patent application publication no. 2015/0297199, filed Apr. 21, 2014, U.S. patent application publication no. 2015/0005789, filed Aug. 23, 2013, and U.S. patent application publication no. 2013/0214025, filed Mar. 7, 2013, and U.S. patent application publication no. 2014/0131418, filed Nov. 9, 2012, the entire contents of each of which are hereby incorporated by reference herein.

Referring initially to FIG. 1, an endoscopic surgical system, which may be in the form of an endoscopic surgical stapler, is designated surgical stapler 10. In general, the surgical stapler 10 may be utilized in any suitable surgical procedure, such as the resection of tissue in the lung, intestines or other organs, involving the use of brachytherapy. The surgical stapler 10, and/or components thereof, may also be utilized to attach suture, mesh, or other flexible material to tissue.

The surgical stapler 10 includes a handle assembly 20 and an elongated body portion 30 that extends distally from the handle assembly 20 along a longitudinal axis "L." The elongated body portion 30 supports an end effector 100 at a distal end of the elongated body portion 30. The end effector 100 is selectively detachable/attachable from/to the elongated body portion 30 and may be rotatable and/or articulatable relative to the elongated body portion 30. The elongated body portion 30 may be rotatable relative to the handle assembly 20. In some embodiments, the distal end of the elongated body portion 30 may include a quick connector that is controllable via the handle assembly 20 to enable quick connection and/or release of the end effector 100 to/from the elongated body portion 30, for example, to provide a safe operating distance from any radiation source emanating from the fasteners (e.g., radioactive source 146 seen in FIG. 7) described herein.

The handle assembly 20 of the surgical stapler 10 includes a handle housing 22 and one or more actuators 24a, 24b, 24c coupled to the handle housing 22 to enable the end effector 100 to perform one or more functions (e.g., rotation, articulation, firing, etc.). For example, the actuator 24a of the handle assembly 20 is operatively coupled to a drive assembly 26 supported within the handle assembly 20 to fire the end effector 100 of the surgical stapler 10 upon an actuation of the actuator 24a of the handle assembly 20 as described in greater detail below. In some embodiments, the handle assembly 20 may include a directional clutch that prevents the actuator 24a of the handle assembly 20 from retracting until fully squeezed or actuated. Although a manually actuated handle assembly is shown, the handle could be motorized or the end effector can be configured as part of a component that connects to a robotic surgical system.

Figure 3:
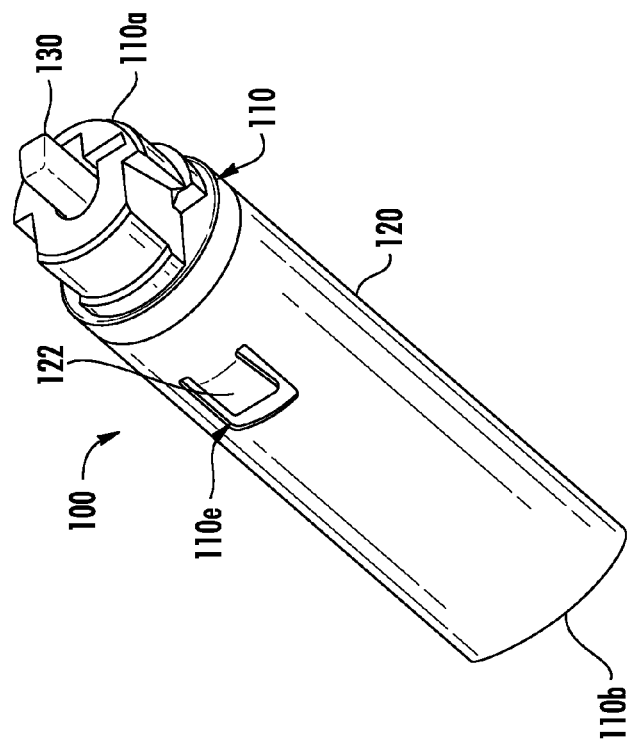
FIG. 3 is a perspective view illustrating a proximal end of the end effector of FIG. 2.
Figure 2:
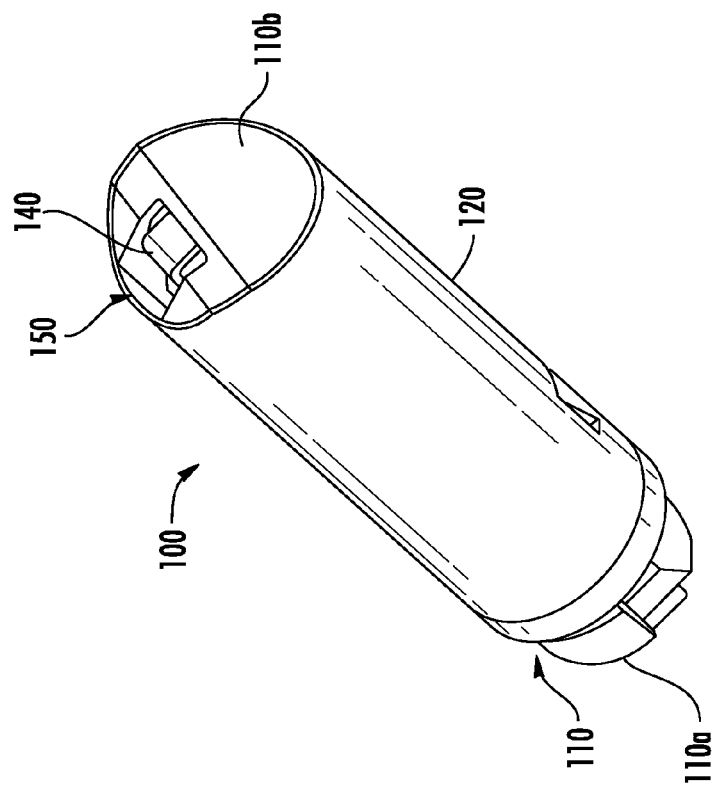
FIG. 2 is a perspective view illustrating a distal end of an end effector of the endoscopic surgical system of FIG. 2.
Figure 4:
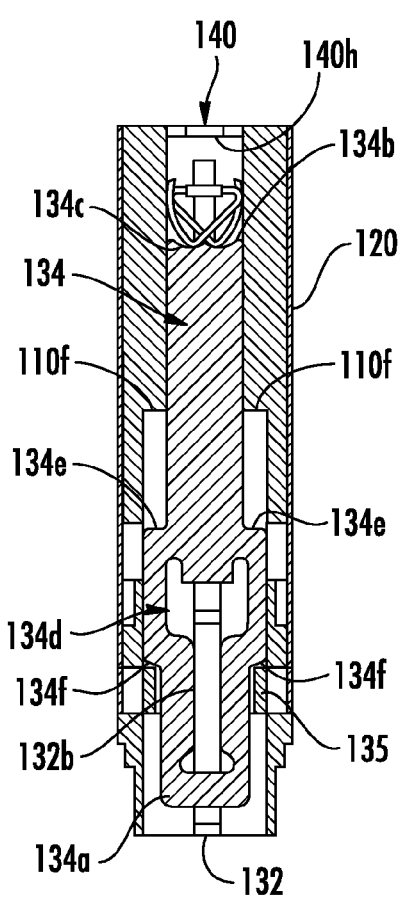
FIG. 4 is a top view of the end effector of FIG. 2 in a first position, the end effector shown with portions thereof removed for clarity.
Figure 5:
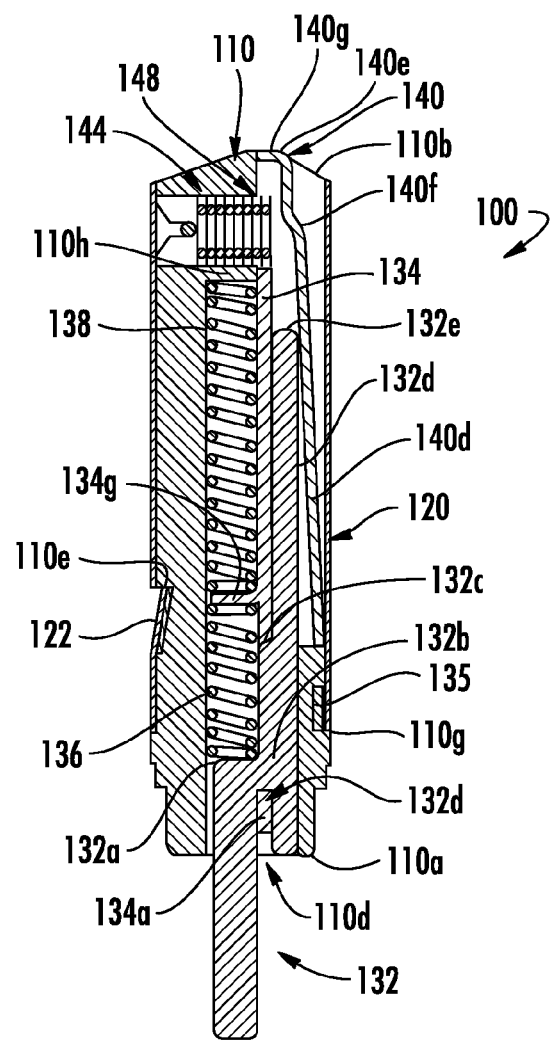
FIG. 5 is a side view of the end effector of FIG. 2 in the first position, the end effector shown with portions thereof removed for clarity.
Figure 6:
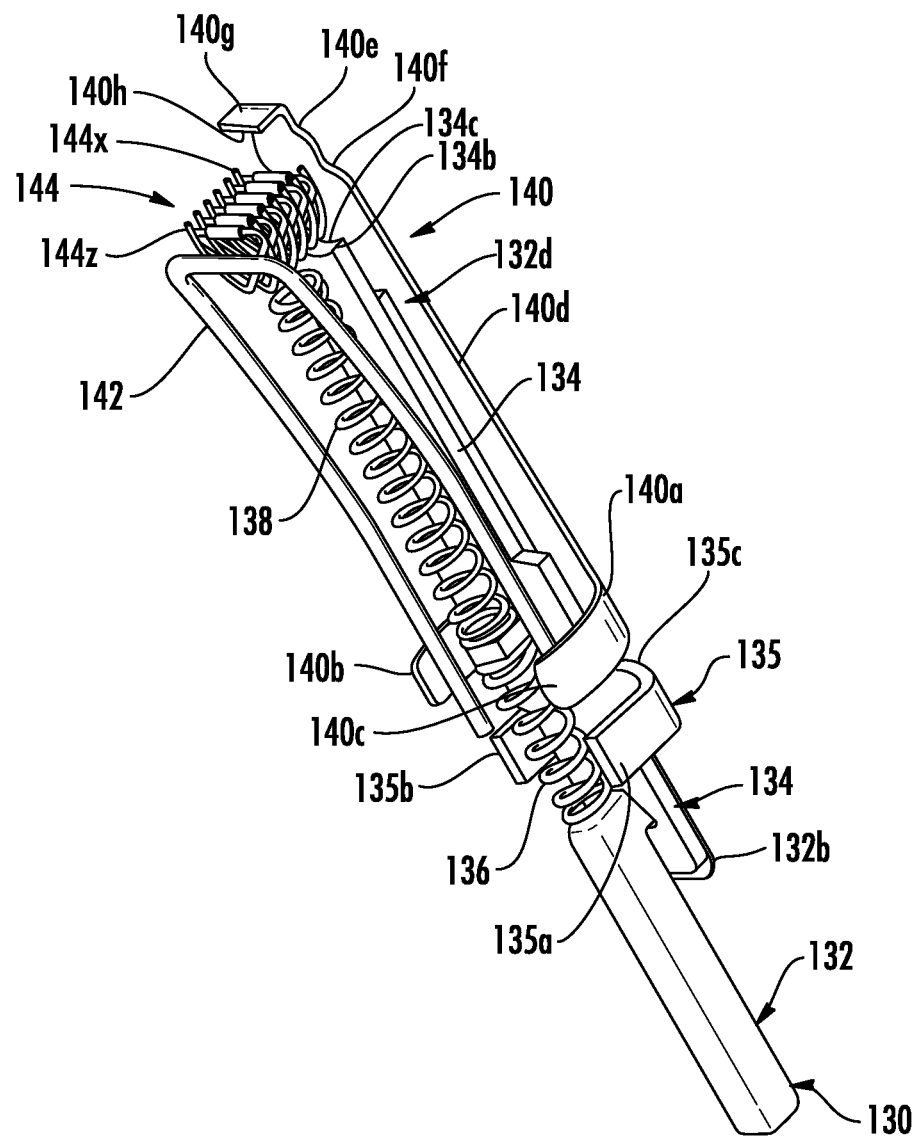
FIG. 6 is a perspective view of a firing assembly of the end effector of FIG. 2.

Turning now to FIGS. 2-6, the end effector 100 of the surgical stapler 10 includes a body 110 having a proximal end 110a and a distal end 110b. The body 110 of the end effector 100 further includes an inner surface 110c defining inner channels 110d that receive a firing assembly 130 of the end effector 100. The proximal end 110a of the body 110 is configured to selectively couple to a distal end of the elongated body portion 30 of the surgical stapler 10. As seen in FIG. 3, the proximal end 110a of the body 110 may be contoured with orientation features, protrusions and/or hooks to provide quick and easy attachment to the distal end of the elongated body portion 30 of the surgical stapler 10. In some embodiments, the proximal end 110a of the end effector 100 may include any suitable mechanical connection such as a snap-on type connection for coupling to the elongated body portion 30 of the surgical stapler 10.

The body 110 of the end effector 100 is supported within an outer sleeve 120 of the end effector 100. The outer sleeve 120 of the end effector 100 includes a tab 122 that extends inwardly to couple the outer sleeve 120 within a notch 110e defined in an outer surface of the body 110 of the end effector 100. The outer sleeve 120 of the end effector 100 may have any suitable diameter such as, for example, 8 mm or smaller to enable passage through a standard 8 mm trocar (not shown) or the like.

The firing assembly 130 of the end effector 100 includes a firing bar 132 that is axially movable within the inner channel 110d of the body 110 of the end effector 100. The firing bar 132 of the firing assembly 130 extends proximally from the end effector 100 and is configured to operatively couple to the drive assembly 26 of the surgical stapler 10. The firing bar 132 extends distally to an abutment wall 132a of the firing bar 132 that connects to a cam fin 132b of the firing bar 132. The cam fin 132b of the firing bar 132 extends distally to drive wall 132c. A cam member 132d of the firing bar 132 is disposed adjacent to the drive wall 132c of the cam fin 132b and extends distally to a camming surface 132e at a distal end of the firing bar 132. The camming surface 132e of the firing bar 132 may be rounded.

The firing assembly 130 of the end effector 100 further includes a pusher 134 coupled to the firing bar 132 of the firing assembly 130. The pusher 134 of the firing assembly 130 includes a proximal end 134a that is received in a recess 132d defined in the firing bar 132 of the firing assembly 130 adjacent to the cam fin 132b of the firing bar 132. The pusher 134 of the firing assembly 130 extends distally to a notch 134c in a distal end 134b of the pusher 134. For example, the notch 134c of the pusher 134 may be W-shaped. The notch 134c may be formed by two U-shaped notches disposed in the same plane adjacent to one another that act as cam forming surfaces for fasteners 144 of the end effector 100 as described in greater detail below. The pusher 134 of the firing assembly 130 further defines an opening 134d that is configured to receive the cam fin 132b of the firing bar 132 therein. The pusher 134 is axially movable within the body 110 of the end effector 100 and selectively engagable with a pusher stop 110f formed in the body 110 distal to front shoulders 134e of the pusher 134. The pusher 134 further includes rear shoulders 134f that are selectively engagable with a retainer clip 135 having opposed arms 135a, 135b coupled by a bridge member 135c. The retainer clip 135 may have a U-shaped configuration. The retainer clip 135 of the end effector 100 is mounted within a clip notch 110g defined in an outer surface of the body 110 of the end effector 100 and is positioned to limit proximal movement of the pusher 134 of the firing assembly 130 upon contact between the rear shoulders 134f of the pusher 134 and the opposed arms 135a, 135b of the retainer clip 135. The pusher 134 also includes a spring tab 134g depending from a bottom surface of the pusher 134.

The firing assembly 130 of the end effector 100 further includes first and second springs 136, 138 that bias the firing bar 132 of the firing assembly 130 and the pusher 134 of the firing assembly 130 proximally. The first spring 136 of the firing assembly 130 may, for example, provide predetermined cam release timing of an anvil 140 of the end effector 100, described in greater detail below. The second spring 138 of the firing assembly 130 may, for example, function to return the pusher 134 of the firing assembly 130 to a proximal or initial position. The proximal end of the first spring 136 is disposed in contact with the abutment surface 132a of the firing bar 132. The distal end of the first spring 136 contacts with a rear surface of the spring partition 134g of the pusher 134. The proximal end of the second spring 138 contacts a front surface of the spring partition 134g and the distal end of the second spring 138 extends distally into contact with a spring stop 110h defined in the body 110 of the end effector 100. A spring rate of the first spring 136 of the firing assembly 130 may be greater than a spring rate of the second spring 138 of the firing assembly 130, whereby the first spring 136 is stronger than the second spring 138. One or both of the first and second springs 136, 138 may be preloaded (e.g., maintained at least partially compressed within the body 110 of the end effector 100).

The anvil 140 of the end effector 100 includes a base member 140a having support legs 140b, 140c. The anvil 140, which may be in the form of a leaf spring, further includes an elongated arm 140d that extends distally from the base member 140a of the anvil 140. The elongated arm 140d of the anvil 140 is connected to a head 140e of the anvil 140 via a transition portion 140f of the anvil 140 disposed at an angle relative to the elongated arm 140d and the head 140e. The head 140e of the anvil 140 includes a lip 140g depending from the head 140c. The lip 140g has a fastener forming surface 140h extending into a firing track 148 of the end effector 100 that is defined in registration with the pusher 134 of the firing assembly 130 and the lip 140g of the anvil 140 of the firing assembly 130.

The firing assembly 130 of the end effector 100 further includes a U-shaped stock spring 142 that extends distally from the retainer clip 135 and is configured to urge the fasteners 144 of the end effector 100 toward the firing track 148 of the end effector 100. The stock spring 142 of the firing assembly 130 supports a stock of fasteners 144 (e.g., six staples) that are individually engagable by the W-shaped notch 134c defined in the distal end 134b of the pusher 134 of the firing assembly 130. The stock spring 142 engages a bottom or last fastener 144z of the stock of unfired fasteners 144 and urges the unfired stock of fasteners 144 into the firing track 148 of the end effector 100 adjacent to the notch 134c of the pusher 134, whereby the stock spring 142 of the end effector 100 functions to load successive unfired fasteners 144 into a firing position within the firing track 148 (e.g., one at a time so that the unfired fasteners 146 can be sequentially fired).

Figure 7:
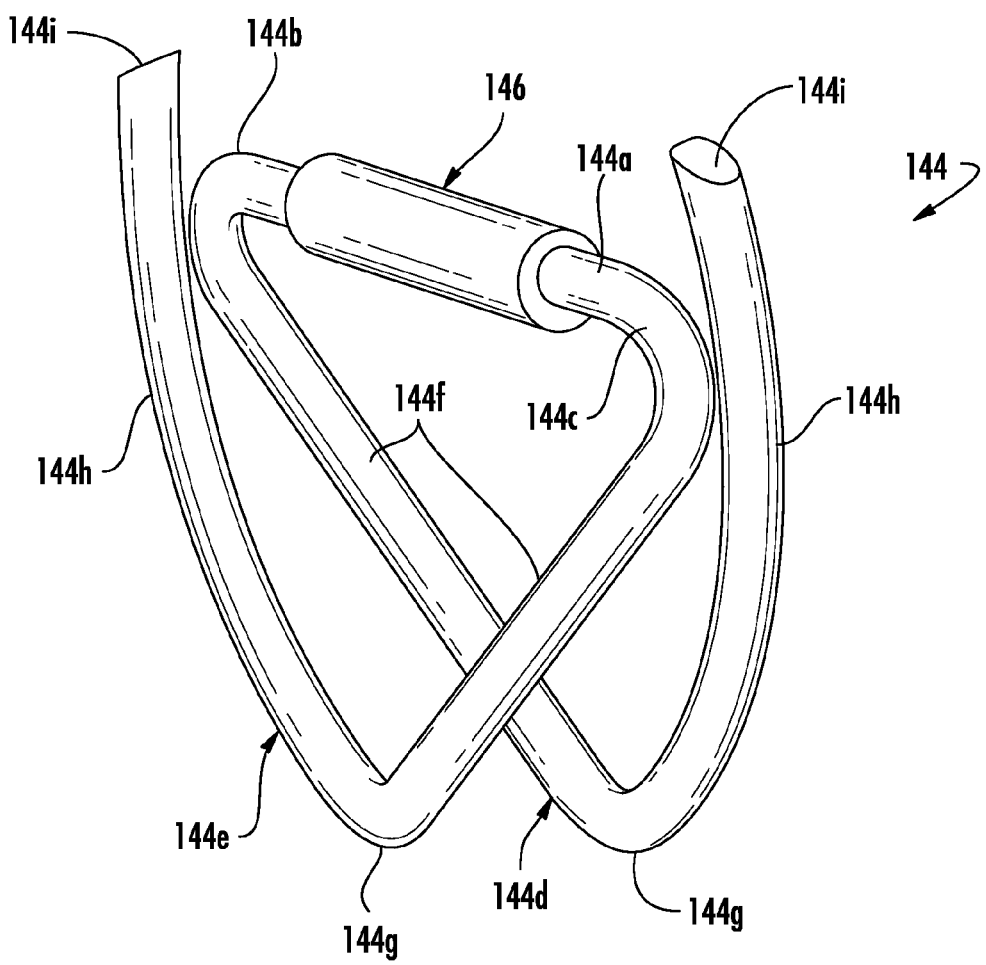
FIG. 7 is a perspective of a fastener of the end effector of FIG. 2, the fastener shown in an unfired state.

As seen in FIG. 7, each fastener 144 of the stock of fasteners 144 includes a backspan 144a that extends to opposite first and second ends 144b, 144c, which may be in the form of elbow segments. Each fastener 144 may have four or more sides "S1-S4" (FIG. 10) while the fastener 144 is in an unformed state. In some embodiments, each fastener 144 may have a W-shaped configuration. The backspan 144a of each fastener 144 may support a radioactive source or isotope 146 (e.g., an isotope capsule) thereon, for example, to effectuate a brachytherapy treatment. The radioactive source 146 of the fastener 144 may be positioned to surround the backspan 144a of the fastener 144 along a central portion of the backspan 144a. The radioactive source 146 of the backspan 144a can include any suitable radioactive isotope, or combinations thereof, such as yttrium-90, cobalt-60, molybdenum-99, lutetium-177, homium-166, iodine-125, iodine-131, palladium-103, samarium-153, phosphorus-32, boron-10, actinium-225, lead 212, etc.

The first end 144b of the backspan 144a hingedly supports a first arm 144d that extends in a first direction and the second end 144c of the backspan 144a hingedly supports a second arm 144e that extends in a second direction that is opposite to the first direction. The first arm 144d of the fastener 144 may include the first end 144b of the backspan 144a and the second arm 144e of the fastener 144 may include the second end 144c of the backspan 144a. In some embodiments, each of the first and second arms 144d, 144e of the fastener 144 may have an L-shaped configuration. Each of the first and second arms 144d, 144e includes a crossing segment 144f, an elbow segment 144g, and a tissue engaging segment 144h that extends to a sharpened tip 144i. Each tissue engaging segment 144h may be inwardly arced with a radius corresponding to a length of its respective crossing segment 144f. The crossing segments 144f of the respective first and second arms 144d, 144e extend from a respective one of the first and second ends 144b, 144c of the backspan 144a. The elbow segment 144g of the respective first and second arms 144d, 144e couples the crossing segments 144f of the respective first and second arms 144d, 144e to the tissue engaging segments 144h of the respective first and second arms 144d, 144e. The tissue engaging segment 144h of the first arm 144d extends in the first direction and the tissue engaging segment 144h of the second arm 144e extends in the second direction such that the tissue engaging segments 144h of the respective first and second arms 144d, 144e extend in opposite directions.

With reference to FIG. 1 and FIGS. 8A-11, the firing bar 132 of the firing assembly 130 is advanced distally along the longitudinal axis "L" of the elongated body portion 30 of the surgical stapler 10, for example, upon an actuation of actuator 24a (e.g., a trigger) of the handle assembly 20 of the surgical stapler 10 relative to the handle housing 22 of the surgical stapler 10. As the firing bar 132 advances distally, illustrated by arrows "A," the abutment wall 132a of the firing bar 132 compresses the first spring 136 of the firing assembly 130 against the spring partition 134g of the pusher 134 of the firing assembly 130. The spring partition 134g of the pusher 134 transmits a driving force to the second spring 138 to compress the second spring 138. As the first and second springs 136, 138 of the firing assembly 130 compress, the pusher 134 of the firing assembly 130 advances distally forward so that the pusher 134 drives an inner-most fastener 144x of the stack of fasteners 144 distally to a first forming position (FIG. 8B and designation "F1" seen in FIGS. 10 and 11) in the firing track 148. In the first forming position of the fastener 144x, the backspan 144a of the fastener 144x, or portions thereof (e.g., the radioactive source 146) engage the fastener formation surface 140h of the lip 140g of the anvil 140 so that the fastener 144x can begin to form. A width of the lip 140g of the anvil 140 is narrower than a width of the backspan 144a of the fastener 144x such that the lip 140g stops the backspan 144a of the fastener 144x from advancing distally while the first and second arms 144d, 144e of the fastener 144x are advanced alongside the lip 140g of the anvil 140.

Also in the first forming position of the fastener 144x, the elbow segments 144g of the respective first and second arms 144d, 144e are received in the notch 134c of the pusher 134 adjacent a center of the notch 134c. Further distal movement of the pusher 134 of the firing assembly 130 toward the lip 1406 of the anvil 140 of the firing assembly 130 drives the elbow segments 144g of the respective first and second arms 144d, 144e against the notch 134c of the pusher 134 and radially away from one another, as illustrated by arrows "C" (see designation "F2" in FIG. 11) without bending the elbow segments 144g of the respective first and second arms 144d, 144e. At the same time, the first and second arms 144d, 144e of the fastener 144x pivot about the respective ends 144b, 144c of the backspan 144a of the fastener 144x in simultaneous circular or radial movement, whereby the ends 144b, 144c of the backspan 144a bend inwardly in a convergent manner. Such simultaneous circular movement of the first and second arms 144d, 144e causes the tissue engaging segments 144h of the respective first and second arms 144d, 144e to approximate one another/converge so that the sharpened tips 144i thereof penetrate and grip tissue "T" disposed adjacent to the fastener 144x. The connector segments 144x of the respective first and second arms 144d, 144e of the fastener 144x also converge toward the backspan 144a of the fastener 144x until the backspan 144a and the connector segments 144x of the respective first and second arms 144d, 144e are parallel, or substantially parallel, to one another (see designation "F3" in FIG. 11) so that the fastener 144x is fully formed, or substantially fully formed. As noted above, the first spring 136 of the firing assembly 130 may have a higher spring constant than the second spring 138 of the firing assembly 130 to provide sufficient cam timing by enabling the fastener 144x of the firing assembly 130 to fully form before the anvil 140 of the firing assembly 130 can separate from the fastener 144x upon engagement with the camming surface 132e of the firing bar 132 of the firing assembly 130.

Figure 10:
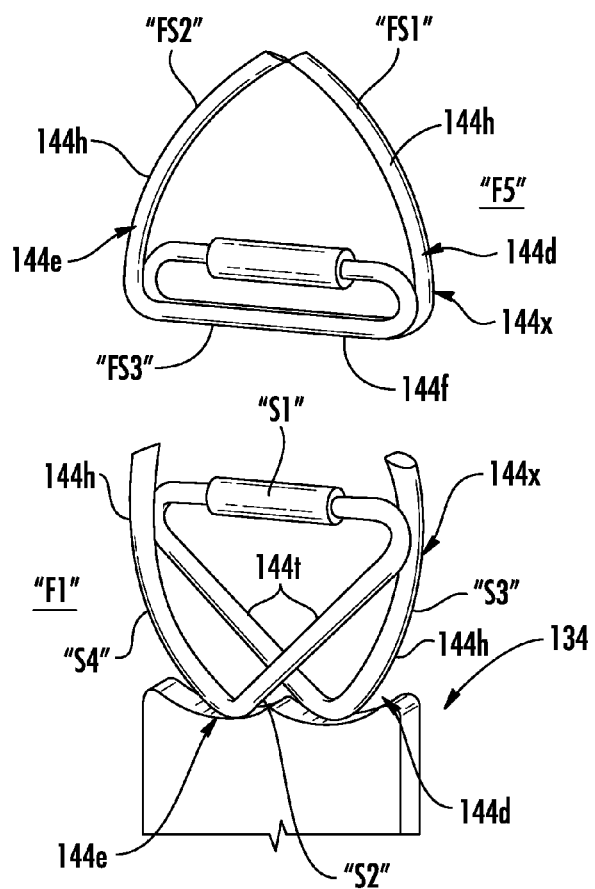
FIG. 10 is an enlarged perspective view of a distal portion of a pusher of the firing assembly of FIG. 6 with the fastener of FIG. 7 shown in the fired and unfired states.
Figure 17:
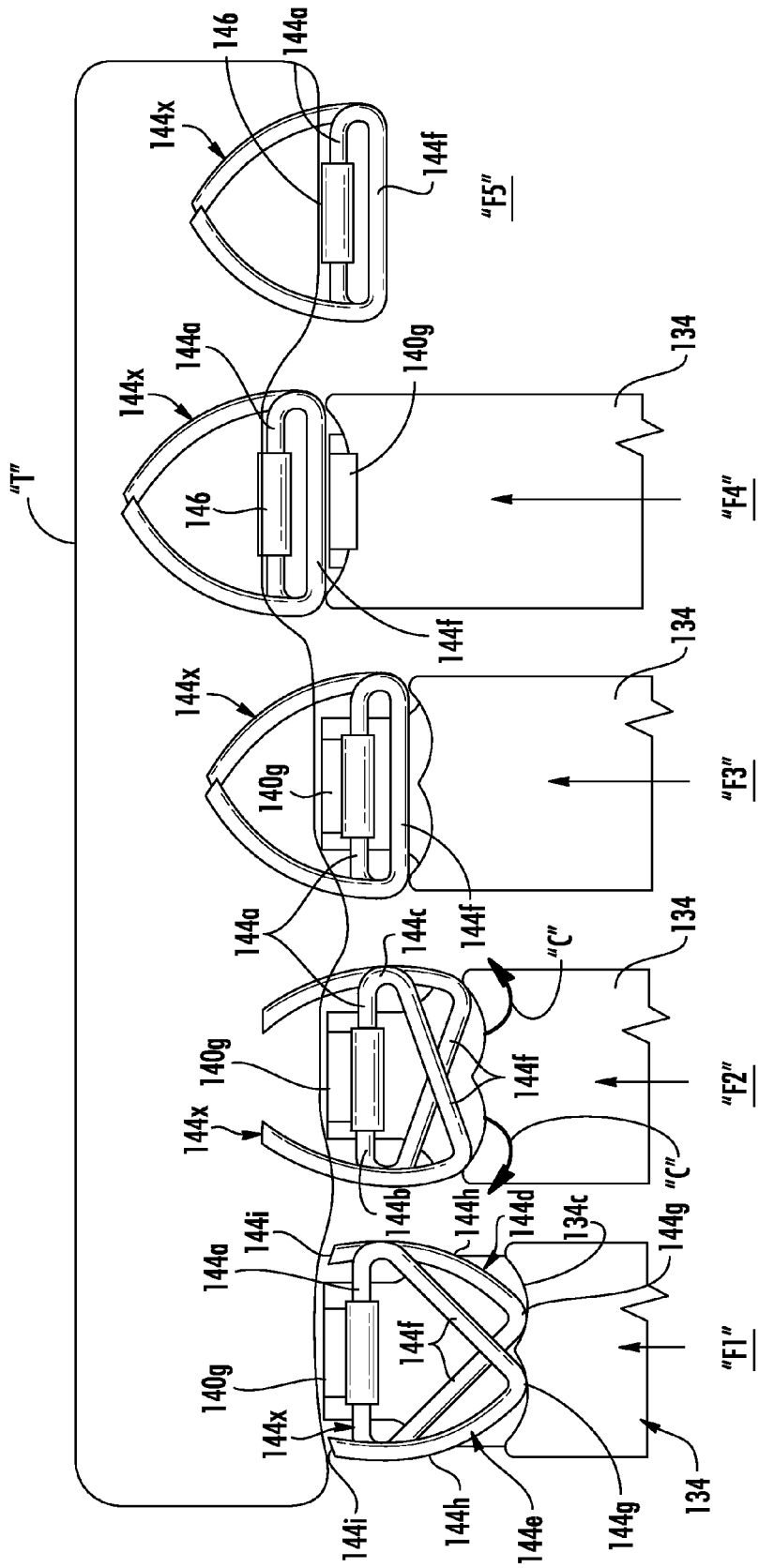

As seen in FIG. 10, as the fastener 144x moves from the unformed configuration having four or more sides "S1-S4" to a fully formed configuration, the number of sides of the fastener 144x may reduce to three sides. In the fully formed configuration of the fastener 144x, the tissue engaging segment 144h of the first arm 144d may define a first formed side "FS1", the tissue engaging segment 144h of the second arm 144e may define a second formed side "FS2", and the connecting segments 144f of the first and second arms 144d, 144e may collectively define a third formed side "FS3." In some embodiments, the fastener 144x, in the fully formed configuration, may have a D-shaped configuration. In some embodiments, the three formed sides "FS1-FS3" of the fastener 144x may surround the backspan 144a and/or the radioactive source 146 supported on the backspan 144a such that the backspan 144a and/or the radioactive source 146 is supported between the three formed sides "FS1-FS3" of the fastener 144x. The radioactive source 146 and/or the backspan 144a may be spaced from the connecting segments 144f of the fastener 144x in both the unformed and formed configurations to limit the risk of damage to the radioactive source 146 during a firing.

Figure 8D:
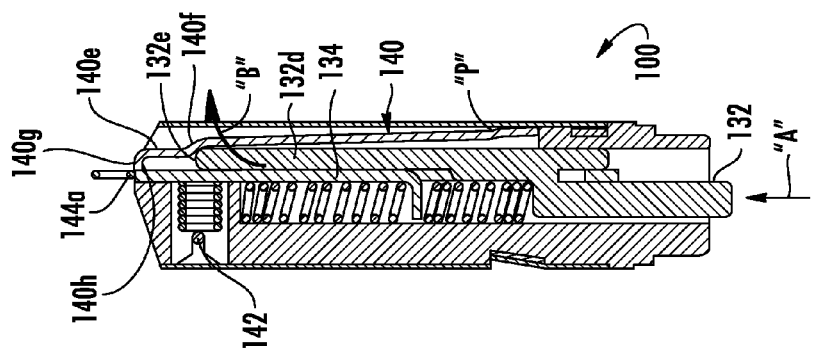
FIGS. 8A-8D are progressive views of the end effector of FIG. 2 illustrating fastener firing.
Figure 8C:
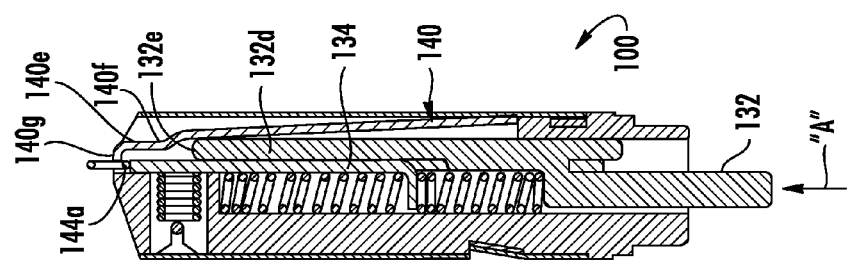
Figure 8B:
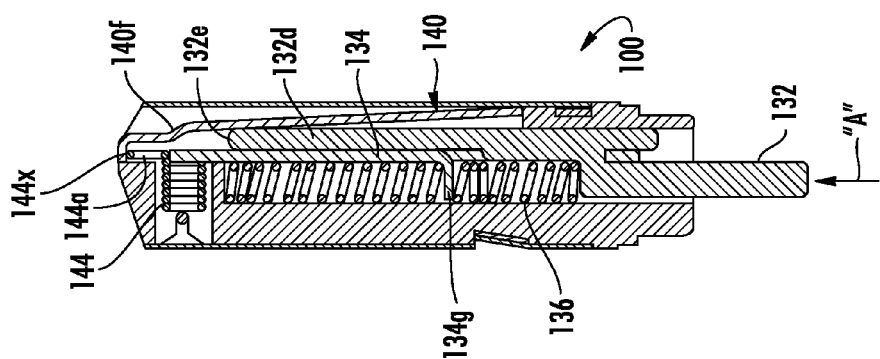
Figure 8A:
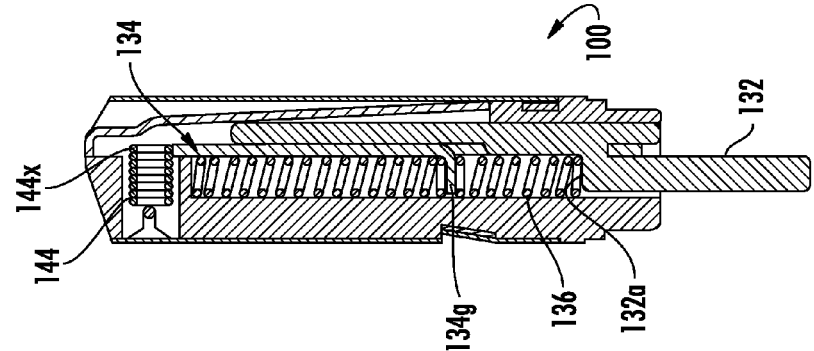
Figure 9:
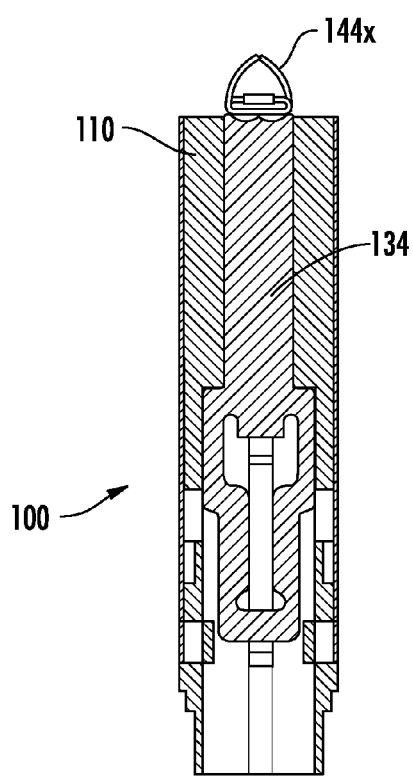
FIG. 9 is a top view of the end effector of FIG. 2 with portions thereof removed for clarity, the end effector shown in a second position with the fastener of FIG. 7 shown in a fired state.

Once the fastener 144x of the stock of unfired fasteners 144 is fully formed or substantially fully formed, the camming surface 132e of the cam member 132d of the firing bar 132 wedges between the pusher 134 and the anvil 140 of the firing assembly 130 to engage the transition portion 140f of the anvil 140 and pivot the anvil 140 about a proximal pivot point "P," as illustrated by arrow "B" (see FIG. 8D). As the anvil 140 of the firing assembly 130 pivots away from the fastener 144x of the stock of unfired fasteners 144, the lip 140g of the head 140c of the anvil 140 separates from the fastener 144x so that the fastener forming surface 140h of the anvil 140 separates from the backspan 144a of the formed fastener 144x. The pusher 134 of the firing assembly 130 continues to distally drive the formed fastener 144x past the lip 140g of the anvil 140 (see designation "F4" in FIG. 11) so that the formed fastener 144x is dispensed from the end effector 100 (see designation "F5" in FIG. 11). In particular, the formed fastener 144x is advanced through a distal opening or fastener exit 150 (see FIG. 2) defined in the body 110 of the end effector 100 and secured to the tissue "T" with the backspan 144a of the formed fastener 144x and/or the radioactive source 146 of the backspan 144a disposed in contacting relation with the tissue "T" (e.g., diseased tissue) to treat the tissue "T."

Once the end effector 100 of the surgical stapler 100 is fired and distal driving forces are released (e.g., actuator 24a released), the first and second springs 136, 138 of the firing assembly 130 bias the pusher 134 and the firing bar 132 of the firing assembly 130 proximal toward their pre-fired or initial positions. With the firing bar 132 of the firing assembly 130 moved or spring-biased proximally, the anvil 140 of the firing assembly 130 biases back to its initial position and the stock spring 142 pushes the remaining unfired fasteners 140 toward the firing track 148 and into registration with the pusher 134 of the firing assembly 130. The end effector 100 of the surgical stapler 10 can then be re-fired and the process repeated as desired until all fasteners 144 are fired. In some embodiments, the end effector 100 can be disposable. In certain embodiments, the end effector 100 is reusable and/or autoclavable. In some embodiments, the sleeve 120 may be removed or adjusted by manipulating the tab 122 thereof to enable additional fasteners 144 to be loaded into the end effector 100 for reuse of the end effector 100.

Figure 12:
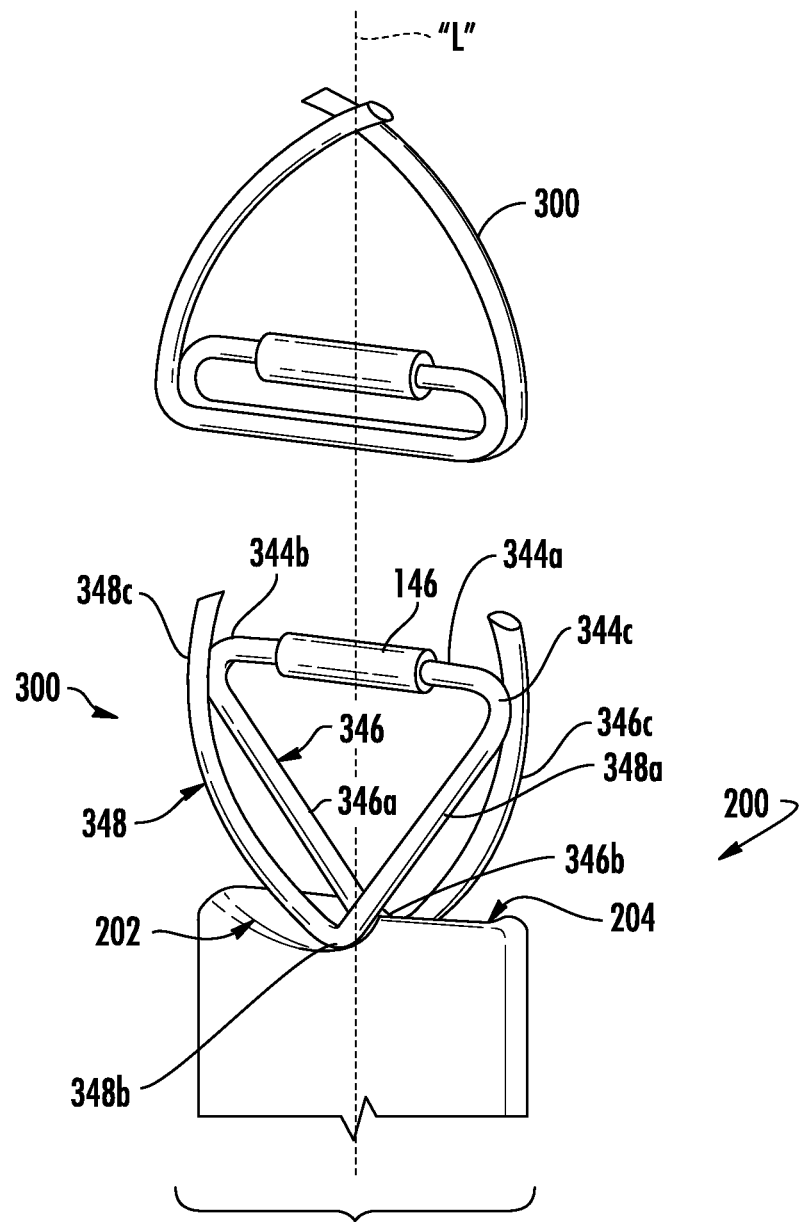
FIG. 12 is a perspective view of another embodiment of a fastener and another embodiment of a pusher of the end effector of FIG. 2.

Turning now to FIG. 12, one embodiment of a pusher, shown generally as pusher 200, may be utilized with end effector 100 to secure to thicker tissue "T." The pusher 200 of the end effector 100 includes first and second notches 202, 204 formed in a distal end thereof. The first and second notches 202, 204 may have U-shaped configurations. The first and second notches 202, 204 of the pusher 200 are supported in different planes that are parallel to one another to enable increased fastener height. The first and second notches 202, 204 of the pusher 200 are also laterally offset from the longitudinal axis "L" in opposite directions of one another.

The pusher 200 of the end effector 100 is configured to receive another embodiment of a fastener 300 of the end effector 100. The fastener 300 of the end effector 100 includes a backspan 344a that extends to opposite first and second ends 344b, 344c. The backspan 344a supports a radioactive source 146 such as an isotope capsule thereon. The first end 344b of the backspan 344a supports a first arm 346 and the second end 344c of the backspan 344a supports a second arm 348. The first and second arms 346, 348 may have an L-shaped configuration. The first arm 346 of the backspan 344a includes a crossing segment 346a, an elbow segment 346b extending from the crossing segment 346a, and a tissue engaging segment 346c extending from the elbow segment 346b. The second arm 348 includes a crossing segment 348a, an elbow segment 348b extending from the crossing segment 348a, and a tissue engaging segment 348c extending from the elbow segment 348b. One or both of the first and second arms 346, 348 of the fastener 300 may be longer than the first and second arms of the fastener 144 in order to accommodate larger tissue thickness and/or an increased volume of radioactive source 146. In some embodiments, one or more of the crossing, elbow, and tissue engaging segments 346a, 346b, 346c of the first arm 346 may be longer than the corresponding crossing, elbow, and tissue engaging segments 348a, 348b, 348c of the second arm 348, or vice-versa.

Any of the presently disclosed embodiments can be configured for single or multi-fire. As noted above, the end effector 100, for example, can be a disposable cartridge or may be reusable/autoclavable and may be selectively removable or reattachable to the surgical stapler 10.

Any of the presently disclosed fasteners, end effectors, and/or surgical staplers may be shipped and/or stored in one or more isolated/protected container (not shown) configured to protect against radiation emanating from the radioactive source.

As can be appreciated, securement of any of the components of the presently disclosed devices can be effectuated using known fastening techniques such welding, crimping, gluing, fastening, etc.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely control the instruments via the robotic surgical system. As can be appreciated, a highly skilled clinician may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the clinician to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the clinician. The scale factor or gearing ratio may be adjustable so that the operator can control the resolution of the working ends of the surgical instrument(s).

The master handles may include various sensors to provide feedback to the clinician relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the clinician with enhanced tactile feedback simulating actual operating conditions. The master handles may also include a variety of different actuators for delicate tissue manipulation or treatment further enhancing the clinician's ability to mimic actual operating conditions.

Figure 13:
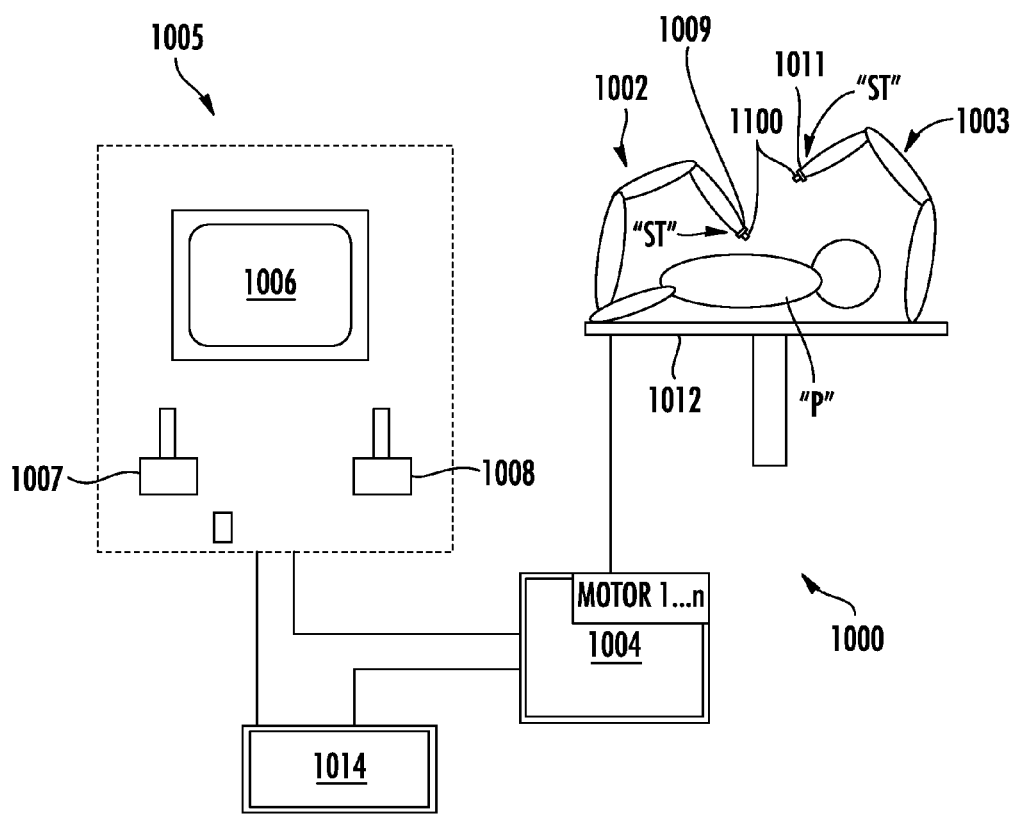
FIG. 13 is a schematic illustration of a medical work station and operating console in accordance with the present disclosure.

Referring also to FIG. 13, a medical work station is shown generally as work station 1000 and generally may include a plurality of robot arms 1002, 1003; a control device 1004; and an operating console 1005 coupled with the control device 1004. The operating console 1005 may include a display device 1006, which may be set up in particular to display three-dimensional images; and manual input devices 1007, 1008, by means of which a person (not shown), for example a clinician, may be able to telemanipulate the robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100 (e.g., a pair of jaw members) in accordance with any one of several embodiments disclosed herein, as will be described in greater detail below.

The robot arms 1002, 1003 may be driven by electric drives (not shown) that are connected to the control device 1004. The control device 1004 (e.g., a computer) may be set up to activate the drives, in particular by means of a computer program, in such a way that the robot arms 1002, 1003, their attaching devices 1009, 1011 and thus the surgical tool (including the end effector 1100) execute a desired movement according to a movement defined by means of the manual input devices 1007, 1008. The control device 1004 may also be set up in such a way that it regulates the movement of the robot arms 1002, 1003 and/or of the drives.

The medical work station 1000 may be configured for use on a patient "P" lying on a patient table 1012 to be treated in a minimally invasive manner by means of the end effector 1100. The medical work station 1000 may also include more than two robot arms 1002, 1003, the additional robot arms likewise connected to the control device 1004 and telemanipulatable by means of the operating console 1005. A surgical system, such as the presently disclosed surgical system, may also be attached to the additional robot arm. The medical work station 1000 may include a database 1014 coupled with the control device 1004. In some embodiments, pre-operative data from patient/living being "P" and/or anatomical atlases may be stored in the database 1014.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. An end effector for a surgical fastening device, the end effector comprising:
   a body defining a longitudinal axis;
   at least one fastener having an unformed configuration and a formed configuration, the at least one fastener including first and second arms, the first and second arms extending in opposite directions and crossing one another in the unformed configuration, the first arm having first and second elbow segments, the first elbow segment configured to bend as the at least one fastener is formed, the second elbow segment configured to remain unbent as the at least one fastener is formed;
   an anvil; and
   a pusher configured to advance the at least one fastener distally through the body and into engagement with the anvil to form the at least one fastener against the anvil.

2. The end effector of claim 1, wherein the anvil is pivotally coupled to the body and movable between a first position and a second position, the anvil configured to engage the at least one fastener while in the first position and to disengage from the at least one fastener while in the second position.

3. The end effector of claim 1, wherein the at least one fastener includes a backspan that extends between the first and second arms, the anvil engagable with the backspan to form the first and second arms about the backspan.

4. The end effector of claim 3, wherein the anvil includes a lip, the lip defining a fastener forming surface configured to contact the backspan so that the first and second arms can pivot about the anvil to form the at least one fastener.

5. The end effector of claim 3, wherein the backspan supports a radioactive source.

6. The end effector of claim 1, further including an anvil release cam that is selectively engagable with the anvil to separate the anvil from engagement with the at least one fastener after the at least one fastener is formed.

7. The end effector of claim 1, wherein the pusher includes a notch formed in a distal end thereof, the notch configured to receive the at least one fastener therein.

8. The end effector of claim 1, further comprising a firing bar, the firing bar axially translatable to axially translate the pusher.

9. The end effector of claim 8, wherein the firing bar and the pusher are spring biased by at least one spring.

10. The end effector of claim 9, wherein the at least one spring includes a first spring and a second spring, the first spring having a different spring rate than the second spring.

11. A fastener for a surgical fastening device, the fastener comprising:
    a backspan having a first end and a second end opposite to the first end, the backspan supporting a radioactive source;
    a first arm extending from the first end of the backspan;
    a second arm extending from the second end of the backspan;
    wherein the first and second arms are movable relative to the backspan from an unformed configuration to a formed configuration, wherein the first and second arms cross in the unformed configuration, and wherein the fastener has more than three sides while the first and second arms are in the unformed configuration and three sides while the first and second arms are in the formed configuration.

12. The fastener of claim 11, wherein each of the first and second arms include a crossing segment and a tissue engaging segment, wherein as the first and second arms are moved from the unformed configuration to the formed configuration, the crossing segments of the first and second arms converge toward the backspan and the tissue engaging segments of the first and second arms converge toward one another.

13. The fastener of claim 11, wherein the crossing segments are connected to the tissue engaging segments of the respective first and second arms by elbow segments.

14. The fastener of claim 11, wherein the radioactive source is supported between the three sides of the fastener when the first and second arms are in the formed configuration.

15. The fastener of claim 14, wherein the radioactive source is in the form of an isotope capsule surrounding the backspan.

16. The fastener of claim 11, wherein the backspan, the first arm, the second arm, or combinations thereof, include titanium wire.

17. A surgical fastening device, comprising:
a handle assembly;
an elongated body portion extending distally from the handle assembly and defining a longitudinal axis; and
an end effector supported on a distal end of the elongated body portion, the end effector including:
a body;
at least one fastener having a backspan and a pair of legs extending from the backspan, the pair of legs crossing one another when in an unformed configuration; and
an anvil that is pivotable between a first position and a second position, the anvil configured to selectively engage the backspan of the at least one fastener to form the at least one fastener while in the first position, the anvil pivotable to the second position to enable the at least one fastener to dispense from the body after being formed.

18. The surgical fastening device of claim 17, wherein the at least one fastener includes a plurality of stacked fasteners that are positioned for sequential firing.

19. The surgical fastening device of claim 18, further including a pusher defining a notch that is selectively engagable with a pair of elbow segments of each fastener of the plurality of stacked fasteners.

20. The surgical fastening device of claim 17, wherein the backspan of the at least one fastener supports a radioactive source.

\* \* \* \* \*